United States Patent
Neuberger

(10) Patent No.: US 8,876,810 B2
(45) Date of Patent: Nov. 4, 2014

(54) BENIGN PROSTATIC HYPERPLASIA TREATMENT METHOD AND DEVICE

(75) Inventor: Wolfgang Neuberger, Labuan (MY)

(73) Assignee: Biolitec Pharma Marketing Ltd, F.T. Lahuan (MY)

( * ) Notice: Subject to any disclaimer, the term of this patent is extended or adjusted under 35 U.S.C. 154(b) by 1055 days.

(21) Appl. No.: 11/714,370

(22) Filed: Mar. 6, 2007

(65) Prior Publication Data

US 2007/0219601 A1 Sep. 20, 2007

Related U.S. Application Data

(60) Provisional application No. 60/784,007, filed on Mar. 20, 2006.

(51) Int. Cl.
| | |
|---|---|
| *A61B 18/22* | (2006.01) |
| *A61B 18/24* | (2006.01) |
| *A61B 17/00* | (2006.01) |
| *A61B 18/00* | (2006.01) |
| *A61B 18/20* | (2006.01) |
| *A61N 5/06* | (2006.01) |

(52) U.S. Cl.
CPC ....... *A61B 18/24* (2013.01); *A61B 2017/00274* (2013.01); *A61B 2018/00547* (2013.01); *A61B 2018/2005* (2013.01); *A61B 2018/207* (2013.01); *A61B 2018/2272* (2013.01); *A61N 2005/0659* (2013.01)
USPC .............................................. 606/16; 385/31

(58) Field of Classification Search
CPC .................. G02B 6/00–6/54; A61B 18/00547
USPC ......................................... 128/898; 606/2–19
See application file for complete search history.

(56) References Cited

U.S. PATENT DOCUMENTS

| | | | | |
|---|---|---|---|---|
| 4,436,368 | A | * | 3/1984 | Keck .............................. 385/127 |
| 4,732,448 | A | * | 3/1988 | Goldenberg ..................... 385/33 |
| 5,349,590 | A | * | 9/1994 | Amirkhanian et al. ........... 372/6 |
| 5,451,221 | A | * | 9/1995 | Cho et al. .......................... 606/3 |
| 5,769,844 | A | * | 6/1998 | Ghaffari .......................... 606/16 |
| 6,554,824 | B2 | | 4/2003 | Davenport et al. |
| 7,003,206 | B2 | * | 2/2006 | Tankala et al. ................ 385/127 |
| 2003/0130649 | A1 | * | 7/2003 | Murray et al. ..................... 606/3 |
| 2004/0151430 | A1 | * | 8/2004 | Neuberger ....................... 385/31 |

OTHER PUBLICATIONS

Tan and Gilling, Holmium laser prostatectomy, Mini-Review, BJU International, vol. 92, pp. 527-530.

* cited by examiner

*Primary Examiner* — Lynsey Crandall
(74) *Attorney, Agent, or Firm* — Bolesh J. Skutnik; BJ Associates

(57) ABSTRACT

A device and method are provided which achieve tissue ablation as well as tissue coagulation substantially simultaneously during the treatment of BPH by utilizing at least two wavelengths of light. The device and method improve urinary flow and minimize post-treatment blood loss and edema while maintaining a nearly blood-free operating field during treatment by irradiating substantially simultaneously with at least two different wavelengths of light. According to the present invention, tissue ablation is affected by having one wavelength that is highly absorbed in the prostatic tissue while another less highly absorbed wavelength coagulates surrounding tissues while maintaining minimal thermal damage to surrounding tissue. In a preferred embodiment the highly absorbed wavelength is about 1460 nm and the less absorbed by water but with some significant hemoglobin absorption is about 980 nm. This combination aids the patient by reducing blood loss and edema. It can aid the practitioner, especially where imaging is employed, by maintaining a substantially blood-free area during treatment. The present device and method is used in conjunction with optical fibers including side emitting optical fibers to provide a practical, minimally invasive treatment of enlarged prostates.

7 Claims, 3 Drawing Sheets

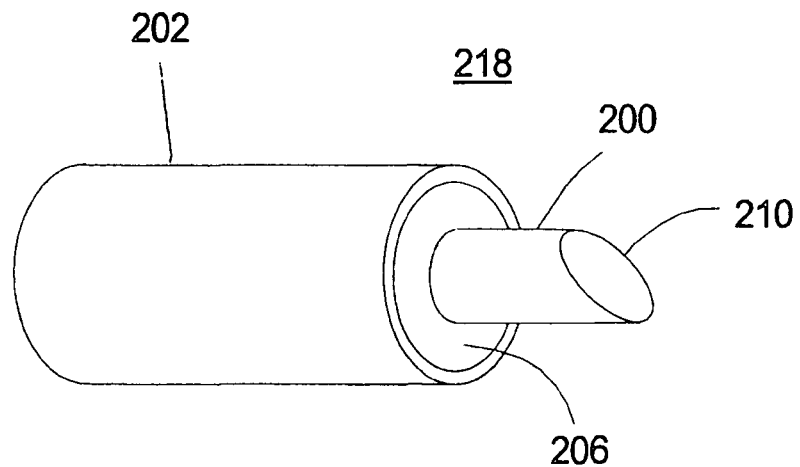
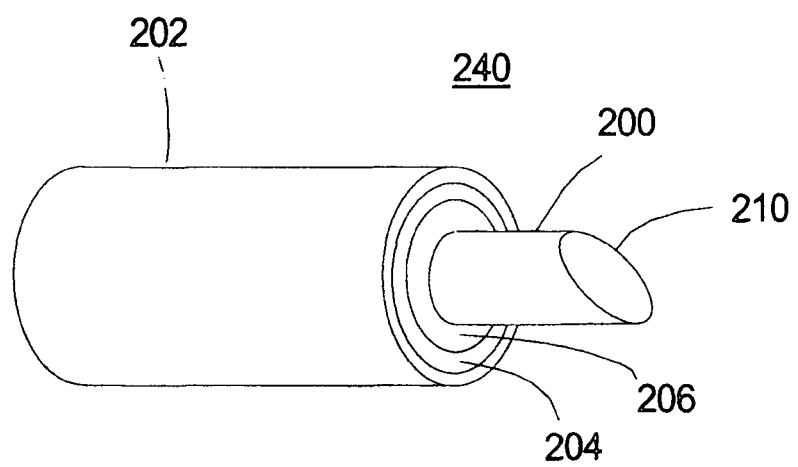

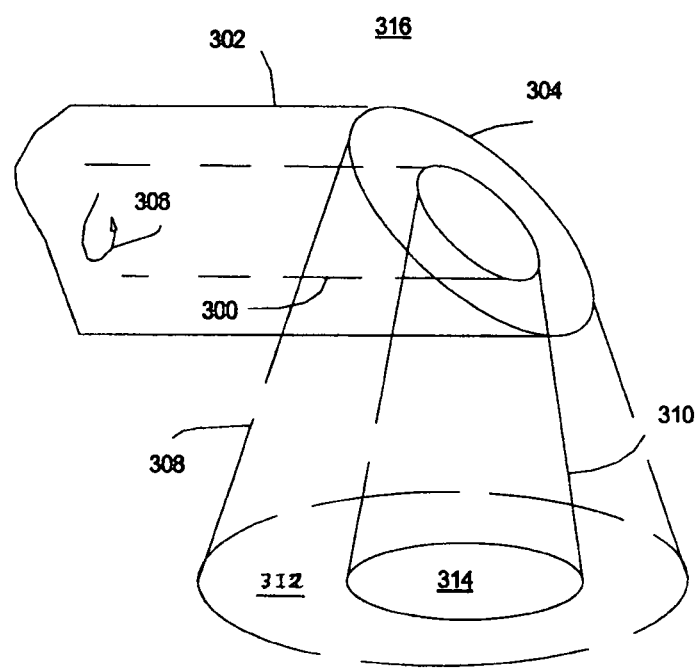

BENIGN PROSTATIC HYPERPLASIA TREATMENT METHOD AND DEVICE

DOMESTIC PRIORITY UNDER 35 USC 119(e)

This application claims the benefit of U.S. Provisional Application Ser. No. 60/784,007 filed Mar. 20, 2006, entitled "Benign Prostatic Hyperplasia Treatment Method and Device" by Wolfgang Neuberger, which is incorporated by reference herein.

BACKGROUND OF THE INVENTION

1. Field of the Invention

The present invention relates generally to devices for treatment of hyperproliferative tissues, and more particularly to a system and method for the treatment of benign prostate hyperplasia that substantially simultaneously ablates excess tissue and coagulates tissue just beyond the ablation, providing a near blood-free treatment, by utilizing at least two or more separate wavelengths of light.

2. Information Disclosure Statement

Benign prostatic hyperplasia (BPH) or "enlarged prostate" refers to the noncancerous (benign) growth of the prostate gland. While BPH is the most common prostate problem in men over 50 years of age, benign growth of the prostate begins with microscopic nodules around 25 years of age but rarely produces symptoms before a man reaches 40. It is estimated that 6.3 million men in the United States have BPH and the disease is responsible for 6.4 million doctor visits and more than 400,000 hospitalizations per year.

The exact cause of BPH is unknown but it is generally thought to involve hormonal changes associated with the aging process. Testosterone likely has a role in BPH as it is continually produced throughout a man's lifetime and is a precursor to dihydrotestosterone (DHT) which induces rapid growth of the prostate gland during puberty and early adulthood. When fully developed, the prostate gland is approximately the size of a walnut and remains at this size until a man reaches his mid-forties. At this point the prostate begins a second period of growth which for many men often leads to BPH later in life.

In contrast to the overall enlargement of the gland during early adulthood, benign prostate growth occurs only in the central area of the gland called the transition zone, which wraps around the urethra. As this area of the prostate grows, the gland presses against the urethra and causes a number of lower urinary tract symptoms (LUTS) such as difficult urination (obstructive symptoms) and painful urination (storage symptoms). Eventually, the bladder itself weakens and loses the ability to empty itself.

Obstructive symptoms such as intermittent flow or hesitancy before urinating can severely reduce the volume of urine being eliminated from the body. If left untreated, acute urine retention can lead to other serious complications such as bladder stones, urinary tract infections, incontinence, and, in rare cases, bladder damage, kidney damage. These complications are more prevalent in older men who are also taking anti-arrhythmic drugs or anti-hypertensive (non-diuretic) medications. In addition to the physical problems associated with BPH, many men also experience anxiety and a reduced quality of life.

Mild symptoms of BPH are most often treated with medication such as alpha-blockers and anti-androgens. Men suffering with moderate to severe BPH symptoms typically must undergo surgery. Transurethral resection of the prostate (TURP) is the standard surgical procedure, although there are a number of other surgical approaches available as well. Other less invasive surgical methods include: transurethral incision of the prostate (TUIP), transurethral microwave thermotherapy (TUMT), transurethral electro vaporization (TUVP), transurethral needle ablation (TUNA), and laser surgery.

There are a number of different laser techniques in which light is used to eliminate excess prostate tissue either by ablation (vaporization) or thermal coagulation mechanisms. The observed clinical effects are due to the absorption of light (by the target tissue itself and/or surrounding fluids) and subsequent heat transfer, the extent of which largely depends on the power and wavelength of the laser beam. In general, wavelength determines the depth of tissue penetration while power has a direct influence on the temperature created within the tissue. However, it is temperature that determines the ultimate impact at the treatment area since tissue must be heated to greater than 50 C to induce coagulation whereas vaporization occurs at temperatures over 100 C. Temperature also impacts morbidity, namely inflammation, dysuria, bleeding, and the need and duration of post-treatment catheterization.

Laser approaches currently in use for the treatment of BPH utilize a single wavelength of light to eliminate excess prostate tissue via ablation or by inducing coagulation necrosis. Initially, however, laser surgeries for BPH used the holmium: YAG laser in combination with the Nd:YAG laser in a treatment method called Combination Endoscopic Laser Prostatectomy (CELAP) being a two step process where the holmium laser was used to create the channel through the prostate and the Nd laser was used for coagulation. It was further determined that the Nd laser was unnecessary if the holmium laser was defocused for coagulation purposes. See A. H. H. Tan and P. J. Gilling, *Holmium Laser Prostatectomy*, BJU International, 92, 527-530 (2003). For the CELAP procedure, the holmium laser was used to create a channel in the prostate by vaporizing the tissue after which, the Nd:YAG laser was used to further eliminate tissue via coagulation. CELAP has been replaced by newer, single-wavelength laser methods which are still being evaluated for long-term efficacy.

Holmium Laser Enucleation of the Prostate or HOLEP is a laser ablation technique in which a 2140 nm Ho:YAG laser is used to remove whole lobes from the prostate. Specifically, HOLEP uses a bare optical fiber which is brought into direct contact with the target tissue. Enucleation occurs when the vapor bubbles that form in front of the fiber bombard the target tissue and tear it apart. Special morcellators or other extraction techniques are needed to remove tissue debris from the area. The efficacy of the HoLEP procedure depends upon maintaining very close contact between the fiber and the tissue to be removed. As a result, it is possible to perforate the prostate during the procedure and many surgeons avoid using HoLEP because of the difficulty in learning and maintaining proficiency in the technique.

Another laser technique to eliminate prostate overgrowth features a frequency-doubled Nd:YAG laser as a pulsed, 532 nm high-power potassium-titanyl-phosphate laser (KTP) that vaporizes target tissue as well as induces thin layers of coagulation in the surrounding tissues as described by Davenport et al. in U.S. Pat. No. 6,554,824. The 532 nm radiation used in KTP is selectively absorbed by hemoglobin and penetrates tissues only to a depth of 1-2 mm. Moreover, this method requires continuous irrigation of the treatment site to cool the tissue during the procedure to help reduce unwanted coagulation necrosis in deeper tissue layers.

Interstitial laser coagulation (ILC) is a minimally invasive method that uses a Nd:YAG laser to reduce the volume of the prostate by inducing coagulation necrosis in the interior of the prostate, as opposed to eliminating tissue via ablation. As a result, ILC does not require the removal of tissue debris during treatment and avoids subsequent sloughing (and associated bleeding) of necrotic tissue post-treatment. However, this wavelength has a relatively long penetration depth and thus has the capacity to produce deeper and broader zones of thermal damage there as necessary. As such, ILC treatment methods require precise, well-controlled positioning and monitoring of the laser fiber tip during the procedure and may only be appropriate for a select group of patients (i.e. patients having a specified pre-operative prostate volume).

Much like TURP, most types of laser surgeries are able to provide an immediate improvement in the urinary stream. Laser surgery for BPH has other potential advantages such as reduced blood loss as well as shorter treatment times, faster patient recovery, and a lower risk of post-treatment incontinence. However, many patients still require catheterization for 1-2 weeks post-treatment after undergoing some forms of laser surgery. Despite the obvious benefits of laser procedures for BPH, long-term follow-up studies on the clinical results of many laser techniques are not yet widely available.

To date, none of the less invasive procedures have proven to be more effective than TURP nor are they generally appropriate across all patient groups including: younger men, debilitated elderly patients, patients with severe medical conditions including uncontrolled diabetes, cirrhosis, active alcoholism, obesity, and heart disease, as well as men taking blood thinning medications. As such, there remains a need for a device and treatment method for the effective alleviation of BPH symptoms that can be used across all patient groups with a minimum of adverse complications post-treatment. The present invention is directed towards this need.

OBJECTIVES AND BRIEF SUMMARY OF THE INVENTION

It is an object of the present invention to provide a device and treatment method that will eliminate a sufficient amount of prostate tissue to improve urinary flow while also minimizing blood loss and edema.

It is another object to provide a fiber optic device and irradiation method utilizing at least two wavelengths of light so as to achieve ablation as well as coagulation in the target tissue.

It is yet another object of the present invention to effectively treat the symptoms of BPH using a fiber optic device and at least two wavelengths of light.

It is still another object to provide a fiber optic device and irradiation method utilizing at least two wavelengths of light to achieve ablation as well as coagulation in the target tissue with a pattern of pulses and energy densities.

Briefly stated, the present invention provides a device and method which achieve tissue ablation as well as tissue coagulation substantially simultaneously during the treatment of BPH by utilizing at least two wavelengths of light, selected to accomplish aforementioned tasks. The device and method improve urinary flow and minimize post-treatment blood loss and edema while maintaining a nearly blood-free operating field during treatment by irradiating substantially simultaneously with at least two different wavelengths of light. According to the present invention, tissue ablation is affected by having one wavelength that is highly absorbed in the prostatic tissue while another less highly absorbed wavelength coagulates surrounding tissues while maintaining minimal thermal damage to surrounding tissue. In a preferred embodiment the highly absorbed wavelength is about 1460 nm and the less absorbed by water but with some significant hemoglobin absorption is about 980 nm. This combination aids the patient by reducing blood loss and edema. It can aid the practitioner, especially where imaging is employed, by maintaining a substantially blood-free area during treatment. The present device and method is used in conjunction with optical fibers including side emitting optical fibers to provide a practical, minimally invasive treatment of enlarged prostates.

The above and other objects, features and advantages of the present invention will become apparent from the following description read in conjunction with the accompanying drawings.

BRIEF DESCRIPTION OF FIGURES

FIGS. 2A and 2B illustrate by perspective views optical fibers of the present invention.

FIG. 3 illustrates by perspective view the application of the optical fiber of FIG. 2 in the medical laser device of FIG. 1.

DETAILED DESCRIPTION OF PREFERRED EMBODIMENTS

Figure 1A:
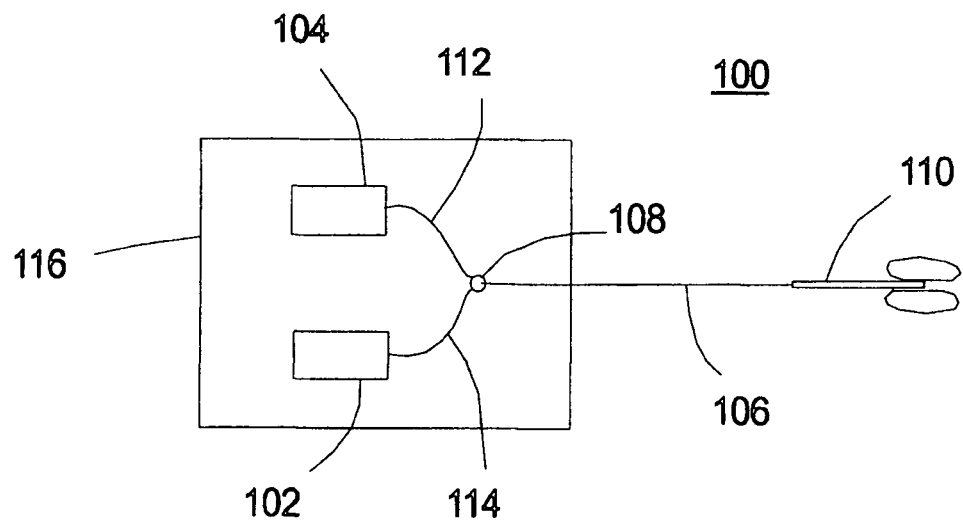
FIGS. 1A and 1B illustrate by block diagrams medical laser devices of the present invention.
Figure 1B:
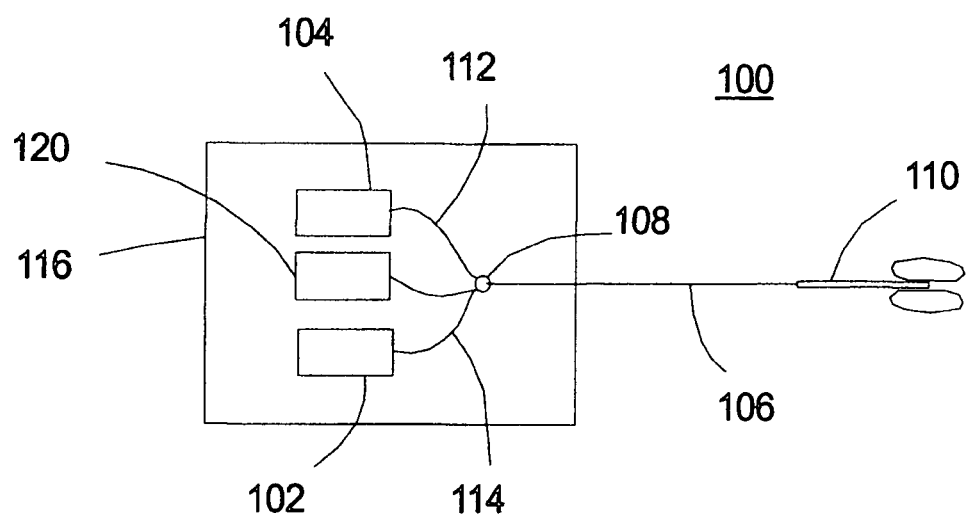

FIG. 1A is a block diagram depicting one embodiment of medical laser device 100 in accord with the present invention. Device 100 includes two laser sources 102 and 104 for the generation of at least two different wavelengths of light. Laser source 102 emits radiation into first optical fiber 114 and laser source 104 emits radiation into second optical fiber 112. A combiner 108 takes the inputs from optical fibers 112 and 114 and forms a single optical fiber 106 that transmits the two different wavelengths of radiation into optical fiber probe 110. According to the present invention, device 100 emits light of at least two different wavelengths, preferably one wavelength is between 980±20 nm and the other is between 1300 nm and 1600 nm. Device 100 further includes a control device 116 where the operational parameters are input. These operational parameters would include power, duration, repetition rate, and continuous or pulse mode, energy density, etc., for each of the lasers therein. FIG. 1B illustrates device 100 having another laser source 120. It is therefore seen that device 100 may have multiple laser sources for performing multiple medical functions necessary to properly treat the illness or condition of concern. These laser sources may be operating at the same time, at different times, in different sequences, with different powers, at different waves, and in different modes.

Probe 110 with attached optical fiber 106 is inserted into the urethra up to the area of the surrounding prostrate tissue of concern by conventional means including catheter. Further other devices may be included in the catheter such as viewing means, irrigating means. Probe 110 would include at least one optical fiber output end for emitting the laser radiation and would have a termination selected from the group consisting of a bare fiber, a capped fiber, and preferably a fiber output end having a side-firing output as well be discussed hereafter.

In a typical mode of operation, probe 110 irradiates the target area with a preselected pattern of pulses and energy densities. Treatment can also involve a semi-continuous irradiation for each position to be treated, or with a turning of the side-firing fiber probe to circumferentially treat a larger section. In preferred embodiments, these patterns of pulses and energy result in the ablation of prostatic tissue as well as coagulation of underlying tissues to substantially eliminate blood loss beyond the removed tissue and with minimal thermal damage to surrounding tissue.

FIGS. 2A and 2B depict a side-emitting tip 210 of probe 110, from FIGS. 1, that may be used in the method of the present invention. In a preferred embodiment, the present invention uses, but is not limited to, a side-emitting tip 210. An exemplary side-emitting fiber is described in U.S. Pat. No. 5,509,917, which is incorporated herein by reference. This reference further discloses means for enclosing the fiber end within a protective cover. The present invention may also employ bare fibers, capped fibers, fibers with shaped or diffusing tips.

In a typical mode of operation, optical fiber 106 delivers laser energy from each laser source and would normally be used in conjunction with a handpiece, endoscope, or similar instrument for positioning the fiber's distal end in close proximity, in direct contact with, or inside/within the target tissue. It is preferred that the handpiece, endoscope, or similar instrument have sufficient channels to accommodate the flow and removal of irrigant and/or debris from the treatment site, endoscopic instruments, aspirators, light guides, image guides, or other sensor and/or detection means.

FIG. 2A illustrates optical fiber 218 having central core 200 for transmitting laser radiation. Cladding layer 206 about core 200 may further transmit laser radiation of a different or same wavelength as core 200. Protective coating 202 being of conventional design and materials encases the cladding layer(s) and the core. In the preferred embodiment, ablative radiation may be directed into central core 200 with the lo coagulating radiation of a different wavelength being directed into cladding layer 206 and/or central core 200. Additional cladding layers may be used as is conventional in the art to protect and guide the optical radiation therein. FIG. 2B illustrates optical fiber 200 with tip 210 having the side-firing device therein. As seen therein, central core 200 includes two cladding layers 206 and 204 with protective coating 202 thereabout. Side-firing tip 316 is shown in greater detail in FIG. 3 and has slanted face 304. Slanted face 304 has an optical coating thereon to reflective all or some of the transmitted radiation. For example, the ablative radiation being in core 300, presently dashed, is reflected off of slanted face 304 into an inner cone 310 of radiation having a smaller cross-section area 314 at the treatment area The coagulating wavelength radiation is conducted in the surrounding or outer layer 302 and is also reflected off of slanted face 304 into an outer cone 308 to form larger cross-section area 312. The characteristics of the radiation emerging from core or one or more of the cladding layers are within the control of control device 116, but as seen in FIG. 3, the coagulating wavelength radiation is in outer cone 308. The coagulating radiation may or may not be in inner cone 310 also.

It is therefore seen that the optical fiber may have one or more cladding layers about the core and that the laser radiation, one wavelength for the ablative effect and the other for the coagulating effect, may be input into the core and also input into the first cladding layer. In the preferred embodiment, the ablative laser radiation, of about 1460 nm, is input into the fiber core and the coagulating laser radiation, of about 980 nm, is input into not only the core but also into a first of the cladding layers. It is also certainly feasible to input the coagulating laser radiation into just the cladding layer, assuming at least two cladding layers are present. It should be understood that either laser emitting these radiations may be operated in the pulsed or continuous mode. In preferred modes the ablation wavelength will generally be pulsed and the coagulation wavelength can be semi-continuous, or pulsed before or during the ablation power pulse.

The present invention is further illustrated by the following examples, but is not limited thereby.

EXAMPLE 1

In accord with the present invention, a medical laser with a maximum average power of 100 W and having an output of two wavelengths of light, the first of which is 980 nm and the second of which is 1460 nm can be used in the treatment of BPH. Lasing can be performed using a 200 µm core diameter, for example, with an all silica optical fiber, for example, with energy in a pulsed mode, for example, using a 50 W of 980 nm radiation and 50 W of 1460 nm radiation in cases where the fiber can be positioned close to the target tissues. The fiber is to be introduced and positioned via a rigid endoscope, for example, with a saline solution as an irrigant.

EXAMPLE 2

In another example, a medical laser with capacity to operate at about 120-150 W at each of two wavelengths of light, has a first wavelength of about 960 nm and a second wavelength of about 1370 nm. Using an all silica optical fiber with a 600 µm core diameter and a 660 µm clad diameter, coagulation can be achieved with a semi-continuous irradiation at 960 nm while ablation is achieved using a semi-pulsed regime for the 1370 nm wavelength. The power at each wavelength would be set at about 120 W. On/off times would be about equal in value and generally about 0.1 of a second or so.

Having described the preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of treating benign prostatic hyperplasia of a prostate comprising the steps of:
    providing a medical laser device having two laser sources therein, said laser sources emitting two wavelengths of radiation;
    selecting a combination of said wavelengths to effect a desired treatment of selected prostatic tissue, wherein the first wavelength provides a coagulating effecting the prostatic tissue, and the second wavelength causes ablation of prostatic tissue;
    delivering said radiation to said selective prostatic tissue by means of an optical fiber having a fiber core and at least one cladding layer;
    positioning an distal end of said optical fiber system in or near said selected prostatic tissue; and
    irradiating said selected prostate tissue of said prostate with said radiation, wherein said first wavelength is transmitted through the at least one cladding layer and said second wavelength is transmitted through said fiber core, wherein said first wavelength transmitted through the at least one cladding layer is shorter than said second wavelength transmitted through said fiber core.

2. A method of treating benign prostatic hyperplasia according to claim 1, wherein said first and said second wavelengths of said radiation are substantially simultaneously delivered.

3. A method of treating benign prostatic hyperplasia according to claim 1, wherein said step of irradiating said selected prostatic tissue includes delivering the first and second wavelengths in a pattern of pulse and energy densities.

4. A method of treating benign prostatic hyperplasia according to claim 1, wherein said first wavelength is 980 (±20) nm and said second wavelength is 1460 (±60) nm.

5. A method of treating benign prostatic hyperplasia according to claim 1 wherein the optical fiber has a distal end selected from the group consisting of a bare fiber, a capped fiber, and a fiber with a shape end.

6. A method of treating benign prostatic hyperplasia according to claim 1 wherein the optical fiber has a distal end that provides side-firing irradiation of said prostatic tissue.

7. A method of treating benign prostatic hyperplasia according to claim 1, wherein said second wavelength of radiation irradiating said selected prostate tissue forms an inner cone surrounded by an outer cone formed by said first wavelength of radiation irradiating said selected prostate tissue.

* * * * *